United States Patent
Chaplais et al.

(10) Patent No.: US 8,637,690 B2
(45) Date of Patent: Jan. 28, 2014

(54) HYBRID ORGANIC-INORGANIC MATERIAL IM-19 AND METHOD OF PREPARING SAME

(75) Inventors: Gerald Chaplais, Mulhouse (FR); Angelique Simon-Masseron, Brunstatt (FR); Joel Patarin, Flaxlanden (FR); Nicolas Bats, Feyzin (FR); Delphine Bazer-Bachi, Saint-Genis-Laval (FR)

(73) Assignee: IFP Energies Nouvelles, Rueil-Malmaison Cedex (FR)

( * ) Notice: Subject to any disclaimer, the term of this patent is extended or adjusted under 35 U.S.C. 154(b) by 555 days.

(21) Appl. No.: 12/919,511

(22) PCT Filed: Feb. 17, 2009

(86) PCT No.: PCT/FR2009/000177
§ 371 (c)(1),
(2), (4) Date: Oct. 19, 2010

(87) PCT Pub. No.: WO2009/115683
PCT Pub. Date: Sep. 24, 2009

(65) Prior Publication Data
US 2011/0028748 A1    Feb. 3, 2011

(30) Foreign Application Priority Data

Feb. 27, 2008  (FR) ..................... 08 01089
Oct. 7, 2008  (FR) ..................... 08 05540

(51) Int. Cl.
*C07F 5/00*    (2006.01)

(52) U.S. Cl.
USPC ............................. 556/1; 502/150

(58) Field of Classification Search
None
See application file for complete search history.

(56) References Cited

FOREIGN PATENT DOCUMENTS

EP    1 674 555 A1    6/2006

OTHER PUBLICATIONS

M. Vougo-Zanda, et al., "Tossing and turning: Guests in the flexible frameworks of metal(III) dicarboxylates," Inorg. Chem. (2008) 47: 11535-11542.*
International Search Report of PCT/FR2009/000177 (Jul. 17, 2009).
C. Volkringer et al., "Synthesis, Crystal Structure and 71 Ga Solid State NMR of a MOF-Type Gallium Trimesate (MIL-96) with μ3-oxo Bridged Trinuclear Units and a Hexagonal 18-Ring Network," Microporous and Mesoporous Materials, vol. 105 (2007) pp. 111-117.
T. Loiseau et al., "A Rationale for the Large Breathing of the Porous Aluminum Terephthalate (MIL-53) Upon Hydration," Chemistry—A European Journal, vol. 10, No. 6 (2004) pp. 1373-1382.

* cited by examiner

*Primary Examiner* — Sudhakar Katakam
(74) *Attorney, Agent, or Firm* — Millen, White, Zelano & Branigan, P.C.

(57) ABSTRACT

The invention relates to a novel hybrid organic-inorganic material containing an inorganic network of metal centers based on the element gallium, connected to each other by organic bridges, to the preparation and to the use thereof. The invention also relates to an intermediate solid obtained during the synthesis of said hybrid organic-inorganic material.

20 Claims, 3 Drawing Sheets

HYBRID ORGANIC-INORGANIC MATERIAL IM-19 AND METHOD OF PREPARING SAME

FIELD OF THE INVENTION

Figure 1:
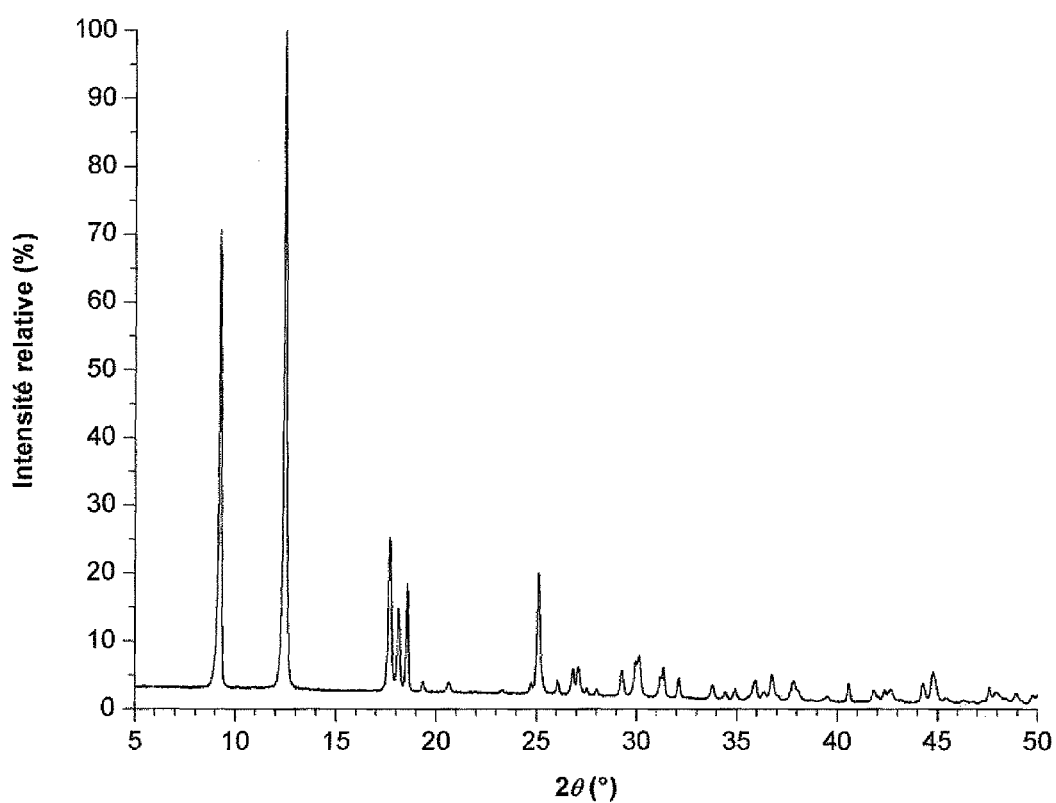

The invention relates to a novel crystallized hybrid material having a mixed organic-inorganic matrix, referred to as IM-19 hereafter, to the preparation method and to the use thereof as catalyst or adsorbent.

BACKGROUND OF THE INVENTION

The porous solid family, of unquestionable significance in everyday life applications as well as industrial applications, still arouses major interest in the research work carried out in the sphere of materials.

Inorganic porous solids have been widely studied in order to increase the opening of their structures so as to facilitate access of the reactants to the active site or departure of the products from this active site.

Since the 1990s, particular interest is taken in hybrid compounds with a mixed organic-inorganic matrix, thus bringing the number of groups that distinguish the porous material types up to 3: inorganic materials, carbon materials and hybrid materials, also referred to as coordination polymers.

These coordination polymers, of which the first ones were described in the 1960s, are the object of an increasing number of publications. In fact, the excitement around these materials has allowed to reach an already advanced structural diversity in a short time (Férey G., L'actualité chimique, January 2007, No. 304). Conceptually, porous hybrid solids with a mixed organic-inorganic matrix are quite similar to porous solids with an inorganic skeleton. Like the latter, they combine chemical entities by giving birth to a porosity. The main difference lies in the nature of these entities. This difference is particularly advantageous and it provides the versatility of this category of solids. In fact, the pore size becomes, through the use of organic ligands, adjustable by means of the length of the carbon chain. The framework which, in the case of inorganic porous materials, could accept only some elements (Si, Al, Ge, Ga, possibly Zn) can, in this case, use all the cations (except the alkaline cations). For these materials, no specific structuring agent is required, the solvent fulfils this function all by itself.

It thus clearly appears that this class of materials allows a multiplicity of structures and, consequently, solids finely suited to the applications they are intended for.

The coordination polymers consist of two elements referred to as connectors and ligands, whose orientation and number of binding sites are determining in the structure of the hybrid material. The diversity of these ligands and connectors gives birth, as already mentioned, to a wide variety of hybrid materials. Other additional auxiliary compounds are also involved in the synthesis: the blockers, counter-ions for example.

What is referred to as ligand is the organic part of the hybrid material. These ligands are, in most cases, di- or tri-carboxylates or pyridine derivatives. Some frequently encountered organic ligands are represented hereafter: bdc=benzene-1,4-dicarboxylate, btc=benzene-1,3,5-tricarboxylate, ndc=naphtalene-2,6-dicarboxylate, bpy=4,4'-bipyridine, hfipbb=4,4'-(hexafluororisopropylidene)-bisbenzoate, cyclam=1,4,8,11-tetraazacyclotetradecane.

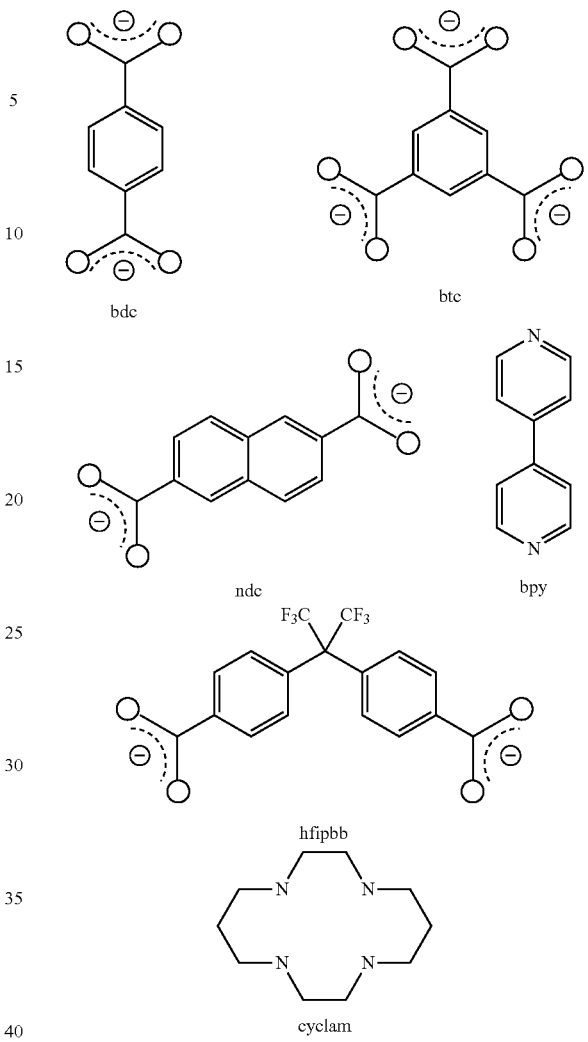

The inorganic entity acting as the connector is a single cation, a dimer, a trimer or a tetramer, or a chain, a plane or even a three-dimensional network.

Yaghi and Férey's teams have thus described a large number of new materials (MOF series and MIL series respectively). Many other teams have followed this path and, today, the number of new materials described is in full expansion. Most often, the studies aim to develop ordered structures exhibiting extremely large pore volumes, good thermal stability and adjustable chemical functionalities.

For example, Yaghi et al. describe a series of boron-based structures in patent US-2006/0,154,807 and they show their relevance in the sphere of gas storage. U.S. Pat. No. 7,202,385 by Mueller et al. provides a particularly complete recapitulation of the structures described in the literature and it perfectly illustrates the multitude of materials that already exist today.

T. Loiseau et al. (*Chem. Eur. J.* 2004, 10, 1373-1382) describe a MIL-53 phase based on aluminium atoms and ligand bdc (benzene-1,4-dicarboxylate). This compound has a three-dimensional structure wherein the one-dimensional inorganic chains with an —Al—O(H)— unit are linked by the deprotonated terephthalic connectors (bdc=$O_2C-C_6H_4-CO_2$). Each aluminium atom is hexacoordinated, two oxygen atoms of the hydroxyl groups being in apical position and four oxygen atoms from four terephthalic connectors being in equatorial position. Furthermore, an organic ligand is linked to four aluminium atoms (two neighbouring aluminium atom pairs). Free terephthalic acid molecules ($H_2bdc=HO_2C-C_6H_4-CO_2H$) occupy the "space left vacant by the framework" with a $H_2bdc/Al$ ratio of 0.7.

By developing a synthesis mode using another type of metal precursor, based on the element gallium, we have obtained a novel hybrid material with a mixed organic-inorganic matrix.

DESCRIPTION OF THE INVENTION

The object of the present invention is a novel hybrid crystallized material referred to as IM-19 with a mixed organic-inorganic matrix, containing an inorganic network of metal centres based on the element gallium, connected to each other by organic ligands of terephthalate type (or bdc) and isostructural to the materials MIL-53.

The hybrid material IM-19 according to the present invention has an X-ray diffraction diagram including at least the lines inscribed in Table 1. This diffraction diagram is obtained by radiocrystallographic analysis using the conventional powder method by means of a STOE STADI-P diffractometer equipped with a front Ge monochromator (111) and a PSD detector. The material analyses were recorded in Debye-Scherrer mode from 5° to 50° (2θ) with a 0.01° resolution (2θ) and a 0.1° pitch for 85 seconds.

The reticular distances $d_{hkl}$ characteristic of the sample are calculated from the position of the diffraction peaks represented by angle 2θ, by applying Bragg's relation. The measuring error $\Delta(d_{hkl})$ on $d_{hkl}$ is calculated as a function of the absolute error $\Delta(2\theta)$ assigned to the measurement of 2θ. An absolute error of $\Delta(2\theta)$ equal to ±0.02° is commonly admitted. The relative intensity $I/I_0$ assigned to each value of $\Delta(2\theta)$ is measured from the height of the corresponding diffraction peak. The X-ray diffraction diagram of the hybrid material IM-19 according to the invention comprises at least the lines at the values of $d_{hkl}$ given in Table 1. In the $d_{hkl}$ column, the mean values of the inter-reticular distances are given in Angström (Å). Each one of these values has to be assigned the value of measuring error $\Delta(d_{hkl})$ ranging between ±0.3 Å and ±0.01 Å.

TABLE 1

Mean $d_{hkl}$ values and relative intensities measured on an X-ray diffraction diagram of hybrid material IM-19

| 2 Theta (°) | $d_{hkl}$ (Å) | $I/I_0$ |
|---|---|---|
| 9.24 | 9.56 | F |
| 12.47 | 7.10 | FF |
| 17.68 | 5.01 | f |
| 18.12 | 4.89 | ff |
| 18.56 | 4.78 | f |
| 19.34 | 4.59 | ff |
| 20.62 | 4.30 | ff |
| 23.29 | 3.82 | ff |
| 24.73 | 3.60 | ff |
| 25.10 | 3.54 | f |
| 26.06 | 3.42 | ff |
| 26.83 | 3.32 | ff |
| 27.09 | 3.29 | ff |
| 27.50 | 3.24 | ff |
| 28.00 | 3.18 | ff |
| 29.25 | 3.05 | ff |
| 29.97 | 2.98 | ff |
| 30.11 | 2.97 | ff |
| 31.19 | 2.87 | ff |
| 31.33 | 2.85 | ff |

TABLE 1-continued

Mean $d_{hkl}$ values and relative intensities measured on an X-ray diffraction diagram of hybrid material IM-19

| 2 Theta (°) | $d_{hkl}$ (Å) | $I/I_0$ |
|---|---|---|
| 32.11 | 2.79 | ff |
| 33.78 | 2.65 | ff |
| 34.42 | 2.60 | ff |
| 34.91 | 2.57 | ff |
| 35.92 | 2.50 | ff |
| 36.36 | 2.47 | ff |
| 36.75 | 2.44 | ff |
| 37.83 | 2.38 | ff |
| 40.56 | 2.22 | ff |
| 41.82 | 2.16 | ff |
| 42.34 | 2.13 | ff |
| 42.65 | 2.12 | ff |
| 44.27 | 2.04 | ff |
| 44.78 | 2.02 | ff |
| 47.59 | 1.91 | ff |
| 47.90 | 1.90 | ff |
| 48.92 | 1.86 | ff | where FF = very high; F = high; m = medium; mf = medium low; f = low; ff = very low. Intensity $I/I_0$ is given with respect to a relative intensity scale where a value of 100 is assigned to the most intense line of the X-ray diffraction diagram: ff < 15; 15 ≤ f < 30; 30 ≤ mf < 50; 50 ≤ m < 65; 65 ≤ F < 85; FF ≥ 85.

FIG. 1 corresponds to the X-ray diffractogram of the hybrid solid IM-19.

The hybrid material IM-19 is indexed in a monoclinic system with, as the cell parameters: a=19.187(3) Å; b=7.628(2) Å, c=6.669(1) Å and angles: α=γ=90°, β=95.86(1)°.

The present invention also relates to a crystallized hybrid material in its as-synthesized form obtained as an intermediate during the preparation of the hybrid material IM-19. This crystallized hybrid material coming in its as-synthesized form is a hybrid material with a mixed organic-inorganic matrix containing a network of metal centres based on gallium, connected to one another by organic ligands of terephthalate type. It exhibits an X-ray diffraction diagram including at least the lines inscribed in Table 2.

This diagram was obtained under the same conditions as those described above for Table 1.

TABLE 2

Mean $d_{hkl}$ values and relative intensities measured on an X-ray diffraction diagram of the intermediate hybrid material in its as-synthesized form

| 2 Theta (°) | $d_{hkl}$ (Å) | $I/I_0$ |
|---|---|---|
| 8.88 | 9.95 | FF |
| 10.15 | 8.71 | FF |
| 12.50 | 7.08 | ff |
| 14.58 | 6.07 | f |
| 15.03 | 5.89 | mf |
| 16.92 | 5.24 | mf |
| 17.80 | 4.98 | FF |
| 18.17 | 4.88 | ff |
| 20.32 | 4.37 | ff |
| 21.16 | 4.20 | f |
| 21.66 | 4.10 | ff |
| 22.54 | 3.94 | ff |
| 24.23 | 3.67 | f |
| 24.99 | 3.56 | ff |
| 26.45 | 3.37 | ff |
| 26.60 | 3.35 | ff |
| 26.83 | 3.32 | m |
| 27.95 | 3.19 | ff |
| 28.39 | 3.14 | ff |
| 30.32 | 2.95 | ff |
| 31.56 | 2.83 | ff |

TABLE 2-continued

Mean $d_{hkl}$ values and relative intensities
measured on an X-ray diffraction
diagram of the intermediate hybrid
material in its as-synthesized form

| 2 Theta (°) | $d_{hkl}$ (Å) | $I/I_0$ |
|---|---|---|
| 32.07 | 2.79 | f |
| 32.45 | 2.76 | ff |
| 32.99 | 2.71 | ff |
| 33.61 | 2.66 | ff |
| 33.93 | 2.64 | ff |
| 34.21 | 2.62 | ff |
| 35.02 | 2.56 | ff |
| 36.04 | 2.49 | ff |
| 39.95 | 2.25 | ff |
| 40.48 | 2.23 | ff |
| 41.34 | 2.18 | ff |
| 41.43 | 2.18 | ff |
| 42.60 | 2.12 | ff |
| 43.08 | 2.10 | ff |
| 43.52 | 2.08 | ff |
| 43.74 | 2.07 | ff |
| 44.16 | 2.05 | ff |
| 45.24 | 2.00 | ff |
| 45.49 | 1.99 | ff |
| 47.43 | 1.92 | ff |
| 47.55 | 1.91 | ff |
| 48.76 | 1.87 | ff | where FF = very high; F = high; m = medium; mf = medium low; f = low; ff = very low. Intensity $I/I_0$ is given with respect to a relative intensity scale where a value of 100 is assigned to the most intense line of the X-ray diffraction diagram: ff < 15; 15 ≤ f < 30; 30 ≤ mf < 50; 50 ≤ m < 65; 65 ≤ F < 85; FF ≥ 85.

Figure 2:
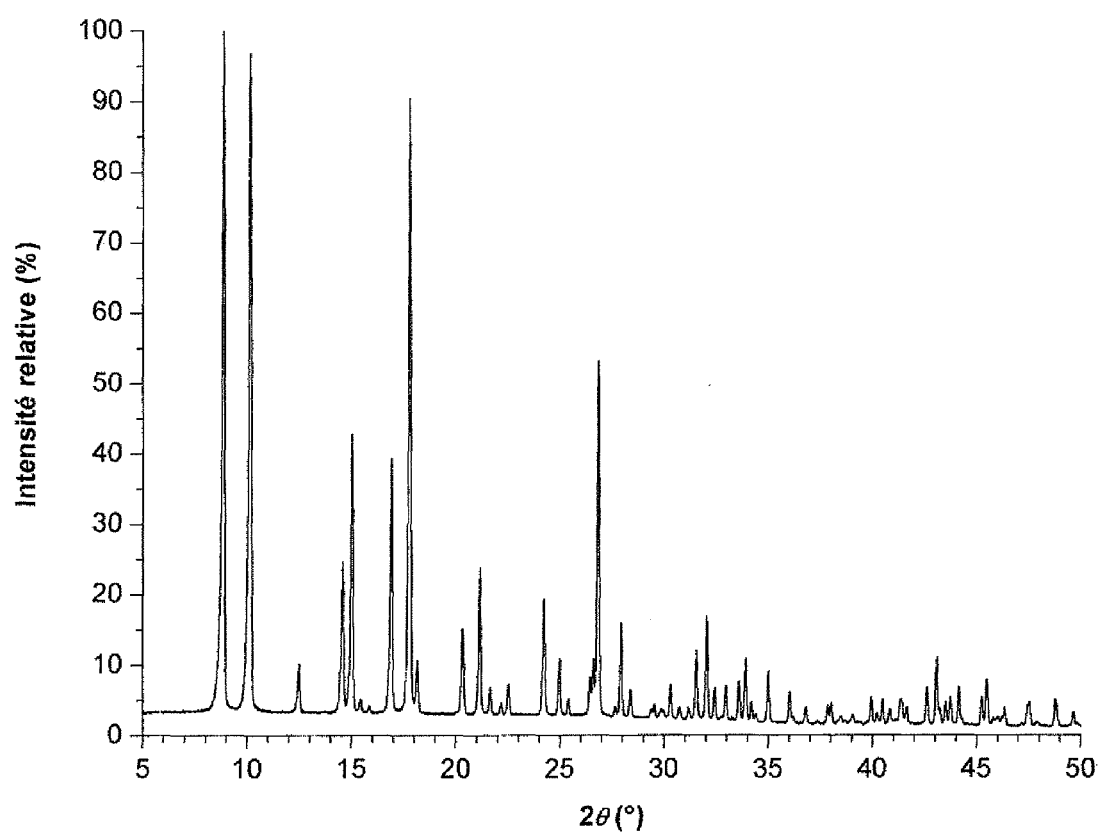
Figure 3:
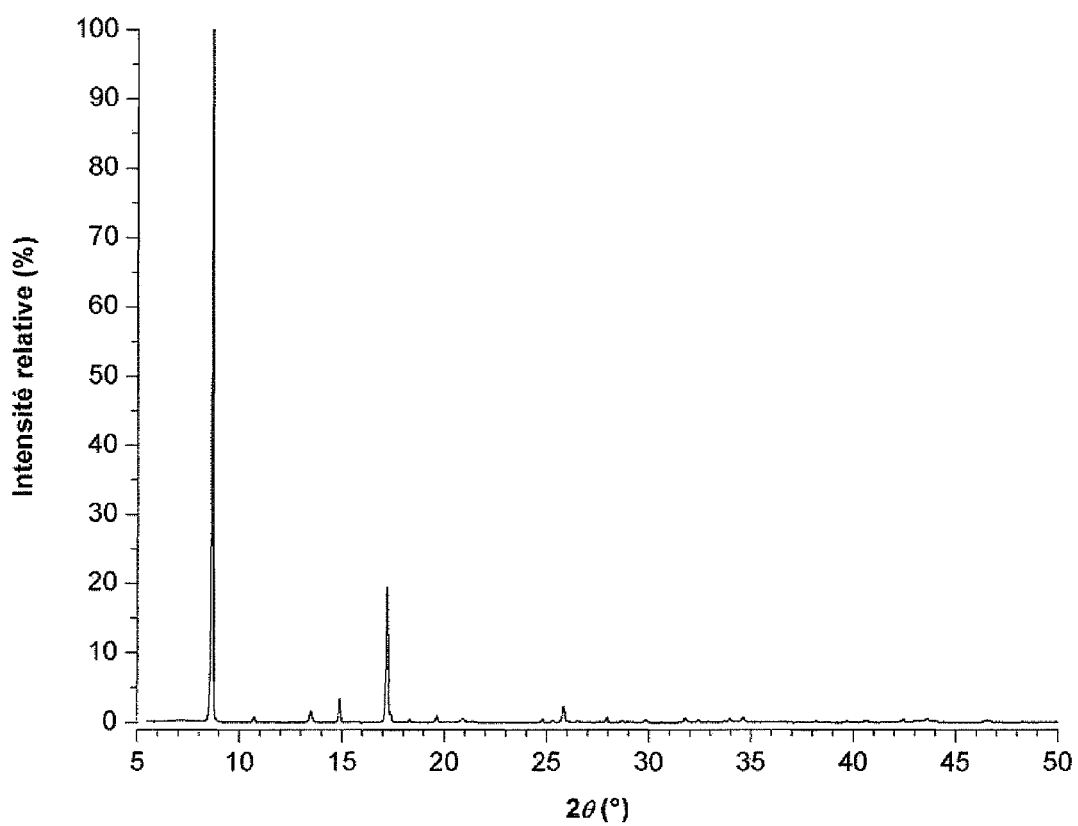

FIG. 2 corresponds to the X-ray diffractogram of the crystallized intermediate solid in its as-synthesized form obtained upon preparation of the hybrid material IM-19.

The as-synthesized crystallized intermediate material is indexed in an orthorhombic system with, as the cell parameters: a=17.422(2) Å; b=12.146(2) Å, c=6.737(1) Å and angles: $\alpha=\gamma=\beta=90°$.

The present invention also describes the method of preparing the crystallized hybrid material IM-19 with a mixed organic-inorganic matrix. This method comprises at least the following stages:

i) dissolving at least one gallium precursor in water,
ii) adding terephthalic acid ($H_2$bdc),
iii) optionally adding hydrofluoric acid,
iv) crystallizing,
v) filtering, washing, drying so as to obtain a crystallized intermediate solid in its as-synthesized form,
vi) activating said as-synthesized crystallized intermediate solid, comprising successively a first stage a) carried out through solvothermal route, at a temperature ranging between 120° C. and 220° C., in the presence of a polar solvent selected from among dimethylsulfoxide (DMSO) and dimethylformamide (DMF), a second stage b) of exchange in the presence of an alcoholic solvent and a third stage c) consisting in heating to a temperature ranging between 150° C. and 280° C. the solid obtained at the end of stage b),
vii) cooling the activated solid so as to obtain said material IM-19, and
viii) optionally heating the material IM-19 obtained to a temperature ranging between 300° C. and 400° C. so as to obtain a dehydrated, porous and solvent-free material.

The gallium precursor is selected from among gallium (III) salts such as gallium chlorides, sulfates, acetates or nitrates. Most preferably, the precursor used is a gallium nitrate.

The molar composition of the mixture obtained upon preparation of hybrid material IM-19 (stages i) to iii)) can be in the following range: 1 mole gallium precursor: 0.5 to 3 moles terephthalic acid: 0 to 1 mole hydrofluoric acid: 100 moles water.

The mixture obtained at the end of stage iii) is subjected to a hydrothermal treatment until crystallization of the intermediate solid is obtained.

Crystallization stage iv) is carried out at a temperature ranging between ambient temperature and 260° C., preferably between 150° C. and 230° C. for 12 to 72 hours, under autogenous reaction pressure conditions.

Drying according to stage v) of the method for preparing material IM-19 is carried out between 20° C. and up to a temperature of 200° C. Most often, drying is performed between 20° C. and 100° C., preferably between 20° C. and 80° C., for a duration ranging between 1 and 24 hours, most often between 4 and 10 hours.

Advantageously, the solid obtained at the end of the drying stage according to stage v) is washed, advantageously with water, with a hot dimethylformamide (DMF) solution, then with ethanol.

At the end of said stage v) of the method of preparing material IM-19, the as-synthesized crystallized intermediate solid wherein terephthalic acid is present is obtained. The X-ray diffraction diagram of this solid is the one shown in FIG. 2, and corresponding to the mean $d_{hkl}$ values and to the measured relative intensities given in Table 2.

Said crystallized intermediate solid is then activated according to stage vi) so as to release the terephthalic acid contained in its pores and to obtain material IM-19, first in dehydrated form after activation stage c), then in hydrated form after stage vii).

First stage a) of the activation treatment is carried out using the as-synthesized crystallized solid that is fed into an autoclave and brought into the presence of a polar solvent selected from among dimethylsulfoxide (DMSO) and dimethylformamide (DMF), preferably DMF, the molar ratio of polar solvent to as-synthesized crystallized solid, preferably the mass ratio of DMF to as-synthesized solid, ranges between 20 and 200, preferably between 50 and 150. Said stage a) is advantageously carried out at a temperature ranging between 150° C. and 180° C. It is advantageously conducted for a duration ranging between 1 and 10 days, very advantageously between 2 and 10 days, and more advantageously between 4 and 10 days.

Said stage a) is preferably followed by cooling to a temperature ranging between ambient temperature and 50° C., then by filtration and drying of the suspension resulting from said stage a). Drying is preferably carried out at a temperature ranging between 20° C. and 50° C.

It is advantageously carried out for a duration ranging between 8 and 24 hours. A crystallized solid comprising occluded polar solvent molecules is obtained.

Second stage b) of the activation treatment consists in exchanging the polar solvent, preferably DMF, present in the pores of the solid from first stage a) of the activation treatment, for an alcoholic solvent preferably selected from among methanol, ethanol and isopropanol. More preferably, said alcoholic solvent is ethanol. Said second stage generally consists in plunging the solid obtained in said stage a) into said alcoholic solvent, preferably ethanol, with an alcoholic solvent/solid, preferably ethanol/solid mass ratio ranging between 200 and 1000, preferably between 350 and 800. More preferably, said second stage is carried out without stirring. It is conducted at a temperature ranging between ambient temperature and 75° C., preferably at ambient temperature.

A suspension is obtained at the end of said stage b) of the activation treatment, said suspension being preferably filtered, then dried so as to obtain a powder. Drying is performed at a temperature ranging between ambient temperature and 70° C., preferably at ambient temperature, for a duration ranging between 2 and 12 hours.

Third stage c) of the activation treatment consists in heating the solid resulting from said stage b) to a temperature ranging between 150° C. and 280° C., preferably for a duration ranging between 8 hours and 3 days. The material obtained at the end of said third stage c) is dehydrated and free of any solvent.

Material IM-19 is finally obtained by cooling the solid activated according to said stage vi), preferably in air. It comes in hydrated form.

This cooling stage is optionally followed by a stage of heating in air to a temperature ranging between at least 300° C. and 400° C., preferably for 1 day. The material obtained at the end of this stage is dehydrated, free of any solvent and porous. It is a crystallized hybrid material exhibiting an X-ray diffraction diagram that includes at least the lines inscribed in Table 3.

This X-ray diffraction diagram is obtained by radiocrystallographic analysis using the conventional powder method by means of a PANALYTICAL X'PERT PRO MPD diffractometer equipped with a front monochromator with an active length of 2.122 mm. Recording was performed in Bragg-Brentano geometry for an angular domain from 5.5000 to 50.0021° at 2θ for a total duration of 36 minutes and 39 seconds.

TABLE 3

Mean $d_{hkl}$ values and relative intensities measured on an X-ray diffraction diagram of the material obtained at the end of the third stage of the activation treatment

| 2 Theta (°) | $d_{hkl}$ (Å) | I/I$_0$ |
|---|---|---|
| 8.67 | 10.19 | FF |
| 10.78 | 8.20 | ff |
| 13.47 | 6.57 | ff |
| 14.89 | 5.94 | ff |
| 17.21 | 5.15 | f |
| 17.44 | 5.08 | ff |
| 18.35 | 4.83 | ff |
| 19.64 | 4.52 | ff |
| 20.87 | 4.25 | ff |
| 24.85 | 3.58 | ff |
| 25.84 | 3.44 | ff |
| 27.99 | 3.19 | ff |
| 31.79 | 2.81 | ff |
| 32.47 | 2.76 | ff |
| 33.78 | 2.65 | ff |
| 33.98 | 2.64 | ff |
| 34.63 | 2.59 | ff |
| 40.71 | 2.21 | ff |
| 42.53 | 2.12 | ff |
| 43.62 | 2.07 | ff |
| 46.53 | 1.95 | ff | where FF = very high; F = high; m = medium; mf = medium low; f = low; ff = very low. Intensity I/I$_0$ is given with respect to a relative intensity scale where a value of 100 is assigned to the most intense line of the X-ray diffraction diagram: ff < 15; 15 ≤ f < 30; 30 ≤ mf < 50; 50 ≤ m < 65; 65 ≤ F < 85; FF ≥ 85.

This porous material is indexed in an orthorhombic system with, as the cell parameters: a=16.734(3) Å; b=13.282(3) Å, c=6.741 (2) Å and angles: α=γ=β=90°.

This porous material whose X-ray diffraction diagram comprises at least the lines inscribed in Table 3 is possibly obtained by heating between 150° C. and 350° C. the solid obtained at the end of stage a) of the activation treatment.

The present invention also relates to the use of hybrid material IM-19 as adsorbent or as catalyst.

The invention is illustrated by the following examples which are in no way limitative.

EXAMPLES

Example 1

Preparation and Characterization of Hybrid Material IM-19 with a Mixed Organic-Inorganic Matrix According to the Invention (Fluorinated Process)

18.33 g distilled water are placed in a 40-ml inner volume PTFE vessel. 2.66 g hydrated gallium nitrate (Alfa Aesar) are added. The mixture is stirred for 5 minutes using a magnetic agitator. After homogenization, 0.52 g of an aqueous solution of hydrofluoric acid (40 mass %, Riedel de Haën) is added. The solution is stirred for 5 minutes. 1.74 g terephthalic acid (Fluka) is then added. The mixture is stirred for 5 minutes. The molar composition of the mixture obtained is: 1 gallium nitrate:1 terephthalic acid:1 HF:100H$_2$O. The content of the PTFE vessel is then transferred to an autoclave and heated without agitation to 220° C. for 3 days. After cooling, the crystallized solid obtained is washed with water, with a hot DMF solution, then with ethanol. After drying in air at 25° C. for about 6 hours, a crystallized intermediate solid in form of a crystalline powder is obtained, which corresponds to the solid in its as-synthesized form having an X-ray diffraction diagram including at least the lines inscribed in Table 2.

Activation of the crystallized solid is carried out first by heating through solvothermal route the as-synthesized crystallized solid in a DMF solution (autoclave filling ratio: 50%; DMF/crystallized solid mass ratio: 75) to 160° C. for 7 days (manual agitation in the autoclave once a day). After cooling, the suspension obtained is filtered and dried at 25° C. for 12 hours. A solid containing DMF in the pores thereof is obtained. It is plunged into an absolute ethanol solution for 24 hours without agitation in order to carry out the second activation stage (EtOH/solid mass ratio: 500). After filtering and drying at 25° C. for 6 hours, the powder obtained is, in a third stage, heated in air to 220° C. for 24 hours. After cooling in air, a solid product in powder form is obtained, analysed by X-ray diffraction and identified as consisting of crystals of solid IM-19 having an X-ray diffraction diagram including at least the lines inscribed in Table 1.

Example 2

Preparation and Characterization of Hybrid Material IM-19 with a Mixed Organic-Inorganic Matrix According to the Invention (Process without Hydrofluoric Acid)

6.61 g distilled water are placed in a 20-ml inner volume PTFE vessel. 0.96 g hydrated gallium nitrate (Alfa Aesar) is added. The mixture is stirred for 5 minutes using a magnetic agitator. 0.61 g terephthalic acid (Fluka) is then added. The mixture is stirred for 5 minutes. The molar composition of the mixture obtained is: 1 gallium nitrate:1 terephthalic acid:1 HF:100H$_2$O. The content of the PTFE vessel is then transferred to an autoclave and heated without agitation to 160° C. for 1 day. After cooling, the crystallized solid obtained is filtered, washed with water, then with a hot DMF solution, then with ethanol. After drying in air at 25° C. for about 6 hours, a crystallized intermediate solid in form of a crystalline powder is obtained, which corresponds to the solid in its as-synthesized form having an X-ray diffraction diagram including at least the lines inscribed in Table 2.

Activation of the crystallized solid is carried out first by heating through solvothermal route the as-synthesized crystallized solid in a DMF solution (autoclave filling ratio: 50%;

DMF/crystallized solid mass ratio: 75) to 160° C. for 7 days (manual agitation in the autoclave once a day). After cooling, the suspension obtained is filtered and dried at 25° C. for 12 hours. A solid containing DMF in the pores thereof is obtained. It is plunged into an absolute ethanol solution for 24 hours without agitation in order to carry out the second activation stage (EtOH/solid mass ratio: 500). After filtering and drying at 25° C. for 6 hours, the powder obtained is, in a third stage, heated in air to 220° C. for 24 hours. After cooling in air, a solid product in powder form is obtained, analysed by X-ray diffraction and identified as consisting of crystals of solid IM-19 having an X-ray diffraction diagram including at least the lines inscribed in Table 1.

Example 3

Preparation and Characterization of Hybrid Material IM-19, for Various Reaction Mixture Molar Compositions and Reaction Temperatures Examples 1 (syntheses a-e) and 2 (syntheses f-h) are repeated by varying the molar composition of the mixture and/or the reaction temperatures, the other operating conditions remaining identical. These various parameters are described in the table below:

| Synthesis No. | Hydrated gallium nitrate (mole) | Terephthalic acid (mole) | Hydrofluoric acid (mole) | Water (mole) | Temperature (° C.) |
|---|---|---|---|---|---|
| a | 1 | 0.5 | 0.5 | 100 | 180 |
| b | 1 | 0.5 | 1.0 | 100 | 180 |
| c | 1 | 1.0 | 1.0 | 100 | 180 |
| d | 1 | 1.0 | 1.0 | 100 | 200 |
| e | 1 | 2.0 | 1.0 | 100 | 220 |
| f | 1 | 1 | — | 100 | 160 |
| g | 1 | 2 | — | 100 | 160 |
| h | 1 | 3 | — | 100 | 160 |

These solids are synthesized by repeating the experimental protocols described in Examples 1 and 2 respectively.

At the end of the stage of activation and cooling of the activated solid, a crystallized powder consisting of IM-19 crystals is obtained.

The invention claimed is:

1. A crystallized hybrid material IM-19 with a mixed organic-inorganic matrix containing an inorganic network of gallium metal centers connected to each other by terephthalate organic ligands, having an X-ray diffraction diagram including at least the lines inscribed in the table below:

| 2 Theta (°) | $d_{hkl}$ (Å) | $I/I_0$ |
|---|---|---|
| 9.24 | 9.56 | F |
| 12.47 | 7.10 | FF |
| 17.68 | 5.01 | f |
| 18.12 | 4.89 | ff |
| 18.56 | 4.78 | f |
| 19.34 | 4.59 | ff |
| 20.62 | 4.30 | ff |
| 23.29 | 3.82 | ff |
| 24.73 | 3.60 | ff |
| 25.10 | 3.54 | f |
| 26.06 | 3.42 | ff |
| 26.83 | 3.32 | ff |
| 27.09 | 3.29 | ff |
| 27.50 | 3.24 | ff |
| 28.00 | 3.18 | ff |
| 29.25 | 3.05 | ff |
| 29.97 | 2.98 | ff |
| 30.11 | 2.97 | ff |
| 31.19 | 2.87 | ff |
| 31.33 | 2.85 | ff |
| 32.11 | 2.79 | ff |
| 33.78 | 2.65 | ff |
| 34.42 | 2.60 | ff |
| 34.91 | 2.57 | ff |
| 35.92 | 2.50 | ff |
| 36.36 | 2.47 | ff |
| 36.75 | 2.44 | ff |
| 37.83 | 2.38 | ff |
| 40.56 | 2.22 | ff |
| 41.82 | 2.16 | ff |
| 42.34 | 2.13 | ff |
| 42.65 | 2.12 | ff |
| 44.27 | 2.04 | ff |
| 44.78 | 2.02 | ff |
| 47.59 | 1.91 | ff |
| 47.90 | 1.90 | ff |
| 48.92 | 1.86 | ff | where FF = very high; F = high; m = medium; mf = medium low; f = low; ff = very low. Intensity $I/I_0$ is given with respect to a relative intensity scale where a value of 100 is assigned to the most intense line of the X-ray diffraction diagram: ff < 15; 15 ≤ f < 30; 30 ≤ mf < 50; 50 ≤ m < 65; 65 ≤ F < 85; FF ≥ 85.

2. A material as claimed in claim 1, indexed in a monoclinic system with, as cell parameters: a=19.187(3) Å; b=7.628(2) Å, c=6.669(1) Å and angles: α=γ=90°, β=95.86(1)°.

3. A crystallized hybrid material in as-synthesized form with a mixed organic-inorganic matrix containing a network of metal centres based on the element gallium, connected to each other by terephthalate organic ligands, having an X-ray diffraction diagram including at least the lines inscribed in the table below:

| 2 Theta (°) | $d_{hkl}$ (Å) | $I/I_0$ |
|---|---|---|
| 8.88 | 9.95 | FF |
| 10.15 | 8.71 | FF |
| 12.50 | 7.08 | ff |
| 14.58 | 6.07 | f |
| 15.03 | 5.89 | mf |
| 16.92 | 5.24 | mf |
| 17.80 | 4.98 | FF |
| 18.17 | 4.88 | ff |
| 20.32 | 4.37 | ff |
| 21.16 | 4.20 | f |
| 21.66 | 4.10 | ff |
| 22.54 | 3.94 | ff |
| 24.23 | 3.67 | f |
| 24.99 | 3.56 | ff |
| 26.45 | 3.37 | ff |
| 26.60 | 3.35 | ff |
| 26.83 | 3.32 | m |
| 27.95 | 3.19 | ff |
| 28.39 | 3.14 | ff |
| 30.32 | 2.95 | ff |
| 31.56 | 2.83 | ff |
| 32.07 | 2.79 | f |
| 32.45 | 2.76 | ff |
| 32.99 | 2.71 | ff |
| 33.61 | 2.66 | ff |
| 33.93 | 2.64 | ff |
| 34.21 | 2.62 | ff |
| 35.02 | 2.56 | ff |
| 36.04 | 2.49 | ff |
| 39.95 | 2.25 | ff |
| 40.48 | 2.23 | ff |
| 41.34 | 2.18 | ff |

| 2 Theta (°) | $d_{hkl}$ (Å) | I/I$_0$ |
|---|---|---|
| 41.43 | 2.18 | ff |
| 42.60 | 2.12 | ff |
| 43.08 | 2.10 | ff |
| 43.52 | 2.08 | ff |
| 43.74 | 2.07 | ff |
| 44.16 | 2.05 | ff |
| 45.24 | 2.00 | ff |
| 45.49 | 1.99 | ff |
| 47.43 | 1.92 | ff |
| 47.55 | 1.91 | ff |
| 48.76 | 1.87 | ff | where FF = very high; F = high; m = medium; mf = medium low; f = low; ff = very low. Intensity I/I$_0$ is given with respect to a relative intensity scale where a value of 100 is assigned to the most intense line of the X-ray diffraction diagram: ff < 15; 15 ≤ f < 30; 30 ≤ mf < 50; 50 ≤ m < 65; 65 ≤ F < 85; FF ≥ 85.

4. A crystallized hybrid material in as-synthesized form as claimed in claim 3, indexed in an orthorhombic system with, as the cell parameters: a=17.422(2) Å; b=12.146(2) Å, c=6.737(1) Å and angles: α=γ=β=90°.

5. A method of preparing a crystallized hybrid material with a mixed organic-inorganic matrix as claimed in claim 1, comprising at least the following stages:
   i) dissolving at least one gallium precursor in water,
   ii) adding to (i) terephthalic acid (H$_2$bdc),
   iii) optionally adding to (i) hydrofluoric acid,
   iv) crystallizing the mixture in (ii),
   v) filtering, washing, drying the product of (iv) so as to obtain a crystallized intermediate solid in its as-synthesized with a mixed organic-inorganic matrix containing a network of metal centres based on the element gallium, connected to each other by organic ligands of terephthalate type, having an X-ray diffraction diagram including at least the lines inscribed in the table below:

| 2 Theta (°) | $d_{hkl}$ (Å) | I/I$_0$ |
|---|---|---|
| 8.88 | 9.95 | FF |
| 10.15 | 8.71 | FF |
| 12.50 | 7.08 | ff |
| 14.58 | 6.07 | f |
| 15.03 | 5.89 | mf |
| 16.92 | 5.24 | mf |
| 17.80 | 4.98 | FF |
| 18.17 | 4.88 | ff |
| 20.32 | 4.37 | ff |
| 21.16 | 4.20 | f |
| 21.66 | 4.10 | ff |
| 22.54 | 3.94 | ff |
| 24.23 | 3.67 | f |
| 24.99 | 3.56 | ff |
| 26.45 | 3.37 | ff |
| 26.60 | 3.35 | ff |
| 26.83 | 3.32 | m |
| 27.95 | 3.19 | ff |
| 28.39 | 3.14 | ff |
| 30.32 | 2.95 | ff |
| 31.56 | 2.83 | ff |
| 32.07 | 2.79 | f |
| 32.45 | 2.76 | ff |
| 32.99 | 2.71 | ff |
| 33.61 | 2.66 | ff |
| 33.93 | 2.64 | ff |
| 34.21 | 2.62 | ff |
| 35.02 | 2.56 | ff |
| 36.04 | 2.49 | ff |
| 39.95 | 2.25 | ff |
| 40.48 | 2.23 | ff |
| 41.34 | 2.18 | ff |
| 41.43 | 2.18 | ff |
| 42.60 | 2.12 | ff |
| 43.08 | 2.10 | ff |
| 43.52 | 2.08 | ff |
| 43.74 | 2.07 | ff |
| 44.16 | 2.05 | ff |
| 45.24 | 2.00 | ff |
| 45.49 | 1.99 | ff |
| 47.43 | 1.92 | ff |
| 47.55 | 1.91 | ff |
| 48.76 | 1.87 | ff | where FF = very high; F = high; m = medium; mf = medium low; f = low; ff = very low. Intensity I/I$_0$ is given with respect to a relative intensity scale where a value of 100 is assigned to the most intense line of the X-ray diffraction diagram: ff < 15; 15 ≤ f < 30; 30 ≤ mf < 50; 50 ≤ m < 65; 65 ≤ F < 85; FF ≥ 85, vi) activating said as-synthesized solid, comprising successively a first stage a) carried out through solvothermal route, at a temperature ranging between 120° C. and 220° C., in the presence of a polar solvent that is dimethylsulfoxide (DMSO) or dimethylformamide (DMF), a second stage b) of exchanging the product of (a) in the presence of an alcoholic solvent and a third stage c) heating to a temperature ranging between 150° C. and 280° C. a solid obtained at the end of stage b),
   vii) cooling thus activated solid so as to obtain said material IM-19, and
   viii) optionally heating the material IM-19 obtained to a temperature ranging between 300° C. and 400° C. so as to obtain a dehydrated, porous and solvent-free material.

6. A method as claimed in claim 5, wherein the gallium precursor is a gallium (III) salt.

7. A method as claimed in claim 6, wherein the gallium precursor is gallium nitrate.

8. A method as claimed in claim 5, wherein the molar composition of a mixture obtained in stages i) to iii) is in the following range: 1 mole gallium precursor: 0.5 to 3 moles terephthalic acid: 0 to 1 mole hydrofluoric acid: 100 moles water.

9. A method as claimed in claim 5, wherein a mixture obtained at the end of stage iii) is subjected to a hydrothermal treatment until crystallization of intermediate solid is obtained, crystallization taking place between ambient temperature and 260° C. for 12 to 72 hours, under autogenous reaction pressure conditions.

10. A method as claimed in claim 5, wherein drying according to stage v) is carried out between 20° C. and 200° C., for a duration ranging from 1 to 24 hours.

11. A method as claimed in claim 5, wherein the mass ratio of polar solvent to as-synthesized crystallized solid involved during first stage a) of the activation treatment ranges between 20 and 200.

12. A method as claimed in claim 5, wherein stage a) is followed by cooling to a temperature ranging between ambient temperature and 50° C., then filtering and drying of a suspension resulting from stage a).

13. A method as claimed in claim 5, wherein the mass ratio of alcoholic solvent to solid involved in stage b) of the activation treatment ranges between 200 and 1000.

14. A method as claimed in claim 5 wherein, at the end of stage b) of the activation treatment, a suspension is obtained, which is then filtered and dried at a temperature ranging between ambient temperature and 70° C.

15. An absorbent comprising the crystallized hybrid of claim 1.

16. A catalyst comprising the crystallized hybrid of claim 1.

17. A method as claimed in claim 8, wherein a mixture obtained at the end of stage iii) is subjected to a hydrothermal treatment until crystallization of an intermediate solid is obtained, the crystallization stage taking place between ambient temperature and 260° C. for 12 to 72 hours, under autogenous reaction pressure conditions.

18. A method as claimed in claim 17, wherein drying according to stage v) is carried out between 20° C. and 200° C., for a duration ranging from 1 to 24 hours.

19. A method as claimed in claim 18, wherein the mass ratio of polar solvent to as-synthesized crystallized solid involved during first stage a) of the activation treatment ranges between 20 and 200.

20. A method as claimed in claim 19, wherein stage a) is followed by cooling to a temperature ranging between ambient temperature and 50° C., then filtering and drying of a suspension resulting from stage a), drying being carried out at a temperature ranging between 20° C. and 50° C.

* * * * *

UNITED STATES PATENT AND TRADEMARK OFFICE
CERTIFICATE OF CORRECTION

PATENT NO. : 8,637,690 B2 Page 1 of 1
APPLICATION NO. : 12/919511
DATED : January 28, 2014
INVENTOR(S) : Chaplais et al.

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 611 days.

Signed and Sealed this
Twenty-second Day of September, 2015

Michelle K. Lee
*Director of the United States Patent and Trademark Office*